United States Patent [19]
Khon

[11] Patent Number: 5,750,671
[45] Date of Patent: May 12, 1998

[54] METHOD FOR ISOLATING DNA FROM BIOLOGICAL CELLS

[76] Inventor: Trinh Cam Khon, 1739 Aprilsong Ct., San Jose, Calif. 95131

[21] Appl. No.: 748,706

[22] Filed: Nov. 13, 1996

[51] Int. Cl.$^6$ .............................. C07H 21/04; C07H 1/08
[52] U.S. Cl. ........................................... 536/25.4; 536/127
[58] Field of Search ........................ 435/91.1; 536/23.1, 536/25.4, 127

[56] References Cited

FOREIGN PATENT DOCUMENTS

| | | |
|---|---|---|
| 1202439 | 11/1960 | Germany. |
| 1260470 | 7/1962 | Germany. |
| 2217911 | 4/1972 | Germany. |

OTHER PUBLICATIONS

Rodman, TC et al. Exp. Cell Res. 150(2):269–281, Feb. 1984.

Doenecke, Interaction of Polystyrene Sulfonate with Nucleosomes, Biochemistry International, vol. 1, No. 3, pp. 237–244, Sep. 21, 1980.

Tubbert et al., Chromatin and Histones in Mealy Bug Spermatogonia, Experimental Cell Research 85, pp. 205–211, 1974.

Trihn et al., Ionic Strength Dependence of the Stability of Polyelectrolyte Complexes, Die Angewandte Makromolekulare Chemie, vol. 212, No. 3718, pp. 167–179, (1993).

Sambrook et al., Molecular Cloning, (second edition) pp. 14–22, (1989).

Zahn et al., Ein Konservierungs-und Darstellungs-Verfahren für Desoxyribonucleinsäuren unde ihre Ausgangsmaterialien, Biochemische Zeitschrift, vol. 336, pp. 281–298, (1962).

Marmur, A Procedure for the Isolation of Deoxyribonucleic Acid from Micro-organisms, J. Mol. Biol., vol. 3, pp. 208–218, (1961).

*Primary Examiner*—David Saunders
*Assistant Examiner*—F. Pierre VanderVegt
*Attorney, Agent, or Firm*—Webb Ziesenheim Bruening Logsdon Orkin & Hanson, P.C.

[57] ABSTRACT

This invention relates to a method for isolating DNA from biological cells containing protamines. The biological parent material is decomposed using salts with low molecular weight above a critical ionic strength cleaving all ionic bonds between DNA and protamines and polystyrene sulfonic acid (PSA) and/or its derivatives in combination with sodium lauryl sulfate. These substances, together with protamines at pH values ranging from 7.5 to 8.5, form insoluble polyelectrolyte complexes facilitating the release of DNA from its natural complexes which can then be precipitated using ethanol. The method according to the invention is fundamentally different from conventional methods as it uses neither enzymes nor toxic extracting agents such as chloroform or phenol. The method according to the invention is very efficient and non-polluting; it can be carried out easily and yields products with a high degree of purity. As the treatment is very gentle, this method is suitable to purify DNA of very high molecular weight.

6 Claims, No Drawings

METHOD FOR ISOLATING DNA FROM BIOLOGICAL CELLS

FIELD OF THE INVENTION

This invention relates to a method for isolating deoxyribonucleic acid from biological cells containing protamines.

BACKGROUND OF THE INVENTION

Methods available so far for isolating deoxyribonucleic acid (DNA) consist of decomposing or degrading suitably prepared cell material by denaturing agents or enzymatic treatment. The DNA it contains is then liberated from contaminating protamines using phenol, chloroform, formamide or other substances. Removal of said toxic substances requires, in general, several extensive, i.e. time-consuming dialyses. After a final obligatory washing step with ethanol, the purified DNA is rehydrated in a suitable buffer.

In order to isolate naturally occurring polyelectrolytes (e.g. DNA, histones, heparine) the ionic bonds of their complexes with basic proteins (e.g. protamines or histones) have to be cleaved. To achieve this cleavage two different methods have been used. One method is the re-complexation with another polyanion like polystyrene sulfonic acid (PSA) in order to cleave weak ionic bonds between DNA and histones (Donecke, D., (1980) Biochem. Int., 1(3), 237–44 and Tubbert, M. A. et al., (1974)Exp. Cell Res., 85(1), 205–11). More than 99% of complexes between protamines and DNA remain unchanged. In this way a direct re-complexation from protamines with PSA is impossible. This method is useful to isolate histones, but not DNA. The other method is to increase ionic strength above a critical ionic strength by using salts with low molecular weight (e.g. NaCl, $Na_2SO_4$) (Trinh C. K., et al., Ang. Makromol. Chem. (1993), 212, 167 (no. 3718)). By this method all ionic bonds between DNA and basic proteins are cleaved. After cleavage of the ionic bonds the resulting DNA has to be purified as described above.

The purification methods that have been in use up to now (Sambrook, J., Fritsch, E. F., and Maniatis, T., (1989), Molecular Cloning: A Laboratory Manual, Cold Spring Harbour Laboratory, Cold Spring Harbour, N.Y.; Centrale de distribution d'aliments proteiniques Grenoble, DAS 1 202 439, (1960); Zahn, K. et al., Biochem. Z. 336, 281 (1962); Institut G. Roussy, DAS 1 260 470 (1962); Rephamag AG, DOS 2 217 911 (1972); Marmur, J. Mol. Biol., 3, 208 (1961)) have several disadvantages caused, in part, by using the toxic agents mentioned above. In addition to the relatively high costs of the chemicals and enzymes used, a further disadvantage is the very time-consuming process of removing these toxic substances from the DNA to be purified (e.g. by dialysis).

SUMMARY OF THE INVENTION

It is an object of the present invention to overcome the disadvantages mentioned above and to provide a simple and cost-effective method for isolating DNA from biological cells containing protamines. This problem is solved according to the invention by:

(a) adding salts with low molecular weight above a critical ionic strength to cleave all ionic bonds between the DNA and protamines and (b) subsequently reacting polystyrene sulfonic acid and/or its derivatives in combination with sodium lauryl sulfate with the appropriately pre-treated (i.e. washed and/or degreased and dried) biological cells containing protamines (such as fish semen, thymic tissue, bovine lung, etc.) after the parent material was appropriately pre-treated at temperatures from 0° C. to 100° C., preferably 40° C. to 60° C., and at a pH value ranging from 7.5 to 8.5, preferably 7.8 to 8.2 wherein the ratio of the weight of the polystyrene sulfonic acid and/or its derivatives to the dry weight of the cell material is 0.1 to 0.8, preferably 0.3 to 0.5. The deoxyribonucleic acid released in this way is separated from by-products and purified.

DETAILED DESCRIPTION OF THE INVENTION

The present invention includes a method for isolating DNA having the steps of:

(a) adding salts with low molecular weight above a critical ionic strength to cleave all ionic bonds between the DNA and protamines and (b) subsequently reacting polystyrene sulfonic acid and/or its derivatives in combination with sodium lauryl sulfate with the appropriately pre-treated (i.e. washed and/or degreased and dried) biological cells containing protamines (such as fish semen, thymic tissue, bovine lung, etc.) after the parent material was appropriately pre-treated at temperatures from 0° C. to 100° C., preferably 40° C. to 60° C., and at a pH value ranging from 7.5 to 8.5, preferably 7.8 to 8.2, wherein the ratio of the weight of the polystyrene sulfonic acid and/or its derivatives to the dry weight of the cell material is 0.1 to 0.8, preferably 0.3 to 0.5. The deoxyribonucleic acid released in this way is separated from by-products and purified.

Due to the well-known strong ionic binding between DNA and protamines, the decomposing of the biological cells and the recomplexing from polystyrene sulfonic acid and released protamines are possible at first in combination with a low molecular weight salt such as sodium lauryl sulfate. Other preferred salts according to the invention are, for example, sodium chloride or sodium sulfate. This surprising effect conducts to a total decomposing of the cell and a 100% release of the DNA into the solution.

The presence of protamines is essential because yeast or plant cells containing generally no protamines can not be used for the isolation of DNA according to the invention.

Polystyrene sulfonic acid and/or its derivatives in combination with sodium lauryl sulfate can be used for both decomposing the cell and recomplexing the protamines at a pH value ranging from 7.5 to 8.5. When a cell is decomposed through low molecular weight salts, the natural complexes of DNA and protamines are dissolved, and insoluble polyelectrolyte complexes (PEC) are formed from protamines and polystyrene sulfonic acid or its derivatives. The DNA that has remained in solution is then precipitated and sediments together with the polyelectrolyte complexes. Subsequent resolubilization of the DNA allows separating off any contaminants in a single centrifugation step. Thus, a highly pure product will be available after another precipitation with ethanol.

The optimum concentration of PSA and/or its derivatives required for recomplexing protamines should be adapted to the portion of protamines of the biological parent material and may be determined by preparatory experiments.

Suitable derivatives of polystyrene sulfonic acid carry one or several halogen atoms, amino groups, hydroxy groups, carboxyl groups, or branched or unbranched alkyl, alkoxy or acyl residues containing up to 6 carbon atoms, or aralkyl or alkylaryl residues containing up to 9 carbon atoms independently of each other at their aromatic ring and/or in their side chain and must be capable of forming insoluble polyelectrolyte complexes from protamines. One suitable derivative is, for example, polyanethol sulfonic acid.

The method according to the invention can be carried out in a very simple way and has a number of advantages as no toxic reagents are used. This makes it not only non-polluting but also very efficient; several steps of dialysis need not be carried out, which results in saving considerable time and amounts of material. In addition, polystyrene sulfonic acid is an inexpensive reagent.

Furthermore, the method is particularly gentle, and the DNA thus isolated has a very high molecular weight. Another advantage is the product's high degree of purity which is indicated by the quotient of its absorption values $A_{260}/A_{280}$ (ca. 1.93).

The method of the invention therefore stands out against other purifying methods both by its improved efficiency, i.e. reduced material costs, less time and by an improved non-polluting effect. The desired product is treated very gently; it has a very high degree of purity that present methods could only achieve by means of extra expenditure.

Even if no particular importance is attached to treating the deoxyribonucleic acid gently because, for example, it is to undergo subsequent hydrolysis, the absence of normally present residual chemicals simplifies subsequent reprocessing and purification of the products of hydrolysis.

The products of DNA hydrolysis, i.e. the nucleotides, nucleosides, and nucleobases or their derivatives can be used for a plurality of pharmaceutical applications (e.g. as antiarrhythmic agents, cytostatic agents, virostatic agents, etc.). In addition, they are needed for scientific purposes and are therefore traded as fine chemicals. Denatured high-molecular DNA (i.e. >50 kb) is used, for example, as a saturator for applications in molecular biology such as DNA hybridization (e.g. in Southern blots).

The method according to the invention shall now be explained in more detail referring to the examples below.

EXAMPLE 1

Purification of DNA from Calves' Thymus 50 g of thawed calves' thymus are added at room temperature to 1 l of ethanol and homogenized in a high-speed mixer for ca. 12 min. The mixture is filtered through a plaited filter and washed twice, each time with 200 ml of ethanol. The degreased thymus is dried under reduced pressure at 25° C. Yield: 7.2 g of dried, degreased calves' thymus 500 mg of thymus thus obtained are added at room temperature to 225 ml of borax buffer solution I (0.0125 mol/l $Na_2B_4O_7$ set to pH 8 with 10% $H_2SO_4$) and homogenized in a high-speed mixer for 0.5 min. 25 ml of polystyrene sulfonic acid solution (8 g of polystyrene sulfonic acid (Aldrich Co.) and 50 g of sodium lauryl sulfate in 1 l of borax buffer solution I) are added to this mixture. The highly viscous mixture is shaken at 50° C. in a securely plugged 500 ml Erlenmeyer flask on a water-bath vibrator table. Cell debris and PEC (polyelectrolyte complexes from protamines and polystyrene sulfonic acid) is sedimented after 3 hours. While cautiously shaking the mixture, it is mixed with the double volume of ethanol (500 ml), and the sedimented DNA is removed from the solution with a glass rod. Residues of PSA complexes remain in the solution and are visible as a slight haze. The crude DNA is washed twice, each time with 150 ml of ethanol/borax buffer solution I (70/30 v/v) while being shaken on the vibrator table. Afterwards, the DNA is mixed with 500 ml of borax buffer solution I in a 1 l Erlenmeyer flask. The flask is securely plugged and shaken at 50° C. on a waterbath vibrator table until the DNA has dissolved completely. Cell debris and insoluble polyelectrolyte complexes are separated off in a 90-minute centrifugation at 13500 g and 4° C. The dissolved pure DNA remaining in the clear supernatant liquid is sedimented again using the 2.5-fold volume of ethanol, and washed first with 50 ml of ethanol/borax buffer solution II (0.0125 mol/l $Na_2B_4O_7$ set to pH 8 with 10% HCl) (70/30 v/v), then with 25 ml of anhydrous ethanol; it is then dried at reduced pressure at 25° C.

500 mg of thymus yielded 86 mg of highly pure DNA. The molecular weight of the purified DNA was in the range from 20 kb to 480 kb (mean value 250 kb), as determined by pulsed field electrophoresis. (Test conditions during pulsed field electrophoresis: Device: Chef-Dr III. Pulsed Field Electrophoresis Systems, Bio-rad Co.; run time: 16 hours; 1% agarose; 6 V/cm; angle: 120°; switch time: 1–50 sec; in 0.5×TBE buffer (trisborate EDTA); reference substances: low range PFG marker, lambda ladder PFG marker, yeast chromosome PFG marker).

Yield: 17.2% (referred to the degreased dried thymus) $A_{260}/A_{280}$: 1.94

EXAMPLE 2

Purification of DNA from the Semen of Carp 50 g of thawed semen of carp are added at room temperature to 1 l of ethanol and homogenized in a high-speed mixer for about 10 min. The mixture is filtered through a plaited filter and washed twice, each time with 200 ml of ethanol. The degreased semen of carp is dried under reduced pressure at 25° C. Yield: 9.1 g of dried, degreased semen of carp 250 mg of semen thus obtained are added at room temperature to 225 ml of borax buffer solution I (0.0125 mol/l $Na_2B_4O_7$ set to pH 8 with 10% $H_2SO_4$) and homogenized in a high-speed mixer for 0.5 min. 25 ml of polystyrene sulfonic acid solution (4 g of polystyrene sulfonic acid (Aldrich Co.) and 50 g of sodium lauryl sulfate in 1 l of borax buffer solution I) are added to this mixture. The highly viscous mixture is shaken at 50° C. in a securely plugged 500 ml Erlenmeyer flask on a water-bath vibrator table. Cell debris and PEC (polyelectrolyte complexes from protamines and polystyrene sulfonic acid) is sedimented after 2 hours. While cautiously shaking the mixture, it is mixed with the double volume of ethanol (500 ml), and the sedimented DNA is removed from the solution with a glass rod. Residues of PSA complexes remain in the solution and are visible as a slight haze. The crude DNA is washed twice, each time with 150 ml of ethanol/borax buffer solution I (70/30 v/v) while being shaken on the vibrator table. Afterwards, the DNA is mixed with 500 ml of borax buffer solution I in a 1 l Erlenmeyer flask. The flask is securely plugged and shaken at 50° C. on a water-bath vibrator table until the DNA has dissolved completely. Cell debris and insoluble polyelectrolyte complexes are separated off in a 90-minute centrifugation at 13500 g and 4° C. The dissolved pure DNA remaining in the clear supernatant liquid is sedimented again using the 2.5-fold volume of ethanol, and washed first with 50 ml of ethanol/borax buffer solution II (0.0125 mol/l $Na_2B_4O_7$ set to pH 8 with 100 HCl) (70/30 v/v), then with 25 ml of anhydrous ethanol, it is then dried at reduced pressure at 25° C.

250 mg of semen yielded 73.3 mg of highly pure DNA. The molecular weight of the purified DNA was in the range from 20 kb to 560 kb (mean value 290 kb), as determined by pulsed field electrophoresis. (Test conditions during pulsed field electrophoresis: Device: Chef-Dr III, Pulsed Field Electrophoresis Systems, Bio-rad Co.; run time: 16 hours; 1% agarose; 6 V/cm; angle: 120°; switch time: 1-50 sec; in 0.5×TBE buffer (trisborate EDTA); reference substances: low range PFG marker, lambda ladder PFG marker, yeast chromosome PFG marker)

Yield: 29.3% (referred to the degreased dried semen)
$A_{260}/A_{280}$: 1.93

I claim:

1. A method for isolating deoxyribonucleic acid from protamine-containing biological cells that are first washed and/or degreased and/or dried, comprising:

(a) adding to the biological cells a salt with low molecular weight above a critical ionic strength to cleave all ionic bonds between DNA and protamines;

(b) subsequently reacting polystryene sulfonic acid and/or its derivatives with the protamines released from the biological cells at temperatures from 0° C. to 100° C., and at a pH value ranging from 7.5 to 8.5, such that the deoxyribonucleic acid is released, wherein the ratio of the weight of the polystyrene sulfonic acid and/or its derivatives to the dry weight of the biological cells is 0.1 to 0.8; and (c) separating and purifying the released deoxyribonucleic acid.

2. The method according to claim 1, wherein the salt with low molecular weight is selected from the group consisting of lauryl sulfate, sodium chloride, and sodium sulfate.

3. The method according to claim 1 wherein the biological cells are derived from fish semen, thymic tissue, or animal lung tissue.

4. The method according to claim 1 wherein the reaction takes place in a pH value range from 7.8 to 8.2.

5. The method according to claim 1 wherein the reaction takes place in a temperature range from 40° C. to 60° C.

6. The method according to claim 1 wherein the reaction takes place at a weight ratio of 0.3 to 0.5 based on the dry weight of the biological cells used.

* * * * *